(12) United States Patent
Seppälä

(10) Patent No.: US 6,814,072 B1
(45) Date of Patent: Nov. 9, 2004

(54) POWDER INHALER

(75) Inventor: Kari Seppälä, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/959,212

(22) PCT Filed: Apr. 20, 2000

(86) PCT No.: PCT/FI00/00346

§ 371 (c)(1),
(2), (4) Date: Jan. 16, 2002

(87) PCT Pub. No.: WO00/64518

PCT Pub. Date: Nov. 2, 2000

(30) Foreign Application Priority Data

Apr. 23, 1999 (FI) .................................................. 990915

(51) Int. Cl.[7] ............................................ A61M 15/00
(52) U.S. Cl. ............................ 128/203.15; 128/203.12; 604/58
(58) Field of Search ....................... 128/203.12, 203.15, 128/203.23; 604/58

(56) References Cited

U.S. PATENT DOCUMENTS

| 5,033,463 | A | * | 7/1991 | Cocozza ................. 128/203.21 |
| 5,263,475 | A | * | 11/1993 | Altermatt et al. ....... 128/203.15 |
| 5,429,122 | A | * | 7/1995 | Zanen et al. ........... 128/203.15 |
| 5,447,151 | A | | 9/1995 | Bruna et al. |
| 5,503,144 | A | * | 4/1996 | Bacon .................... 128/203.15 |
| 5,542,411 | A | * | 8/1996 | Rex ....................... 128/203.15 |
| 5,579,760 | A | * | 12/1996 | Kohler ................... 128/203.15 |
| 5,617,845 | A | * | 4/1997 | Poss et al. ............. 128/203.15 |
| 5,628,307 | A | * | 5/1997 | Clark et al. ............ 128/203.15 |
| 5,673,685 | A | * | 10/1997 | Heide et al. ........... 128/203.15 |
| 5,975,076 | A | * | 11/1999 | Yianneskis et al. ..... 128/203.15 |
| 5,996,577 | A | * | 12/1999 | Ohki et al. ............. 128/203.15 |
| 6,029,661 | A | * | 2/2000 | Whaley et al. ......... 128/203.15 |
| 6,029,662 | A | * | 2/2000 | Marcon ................. 128/203.15 |

FOREIGN PATENT DOCUMENTS

WO    WO 92/18188    10/1992

* cited by examiner

Primary Examiner—Henry Bennett
Assistant Examiner—Mital Patel
(74) Attorney, Agent, or Firm—Finnegan, Henderson, Farabow, Garrett & Dunner, LLP

(57) ABSTRACT

A device for dispensing powdered medicament by inhalation comprises an axially movable metering rod (3) equipped with a dosing recess in the form of a hole (5). The metering rod (3) extends through the interior of the medicament container (1). In a first position the dosing hole (5) is in the medicament container (1) and is filled with a dose of the powdered medicament. In the second position the filled dosing hole (5) is in the air channel (11). The device of the invention has good metering accuracy, it is not susceptible to jamming and provides complete discharge of the powdered dose into the breathing air even if used by a patient having reduced inhalation capacity.

14 Claims, 4 Drawing Sheets

POWDER INHALER

This application is a national stage filing of PCT International Application No. PCT/FI00/00346, filed on Apr. 20, 2000, which published in the English language. This application also claims the benefit of priority under 35 U.S.C. § 119(a) to Finnish patent application No. 990915, filed on Apr. 23, 1999.

BACKGROUND OF THE INVENTION

The present invention relates to a device for dispensing of a powdered drug preparation by inhalation. The device is in particular a multiple-dose device without propellant gas, equipped with a metering means which dispenses doses from a powder container. The device of the invention is useful, for example, in the treatment of asthma.

The administering of a powdered drug preparation by inhalation from an inhaler is known. Multidose type powder inhalers comprising a drug container and a metering member for measuring and dispensing a unit dose are also known, for example from patent publications GB 2165159, EP 79478, and EP 166294. In these devices, a series of dosing recesses are notched into the surface of a cylindrical metering member, and the said member is disposed in a chamber of precisely the same shape. When the metering member is rotated, the dosing recesses in turn will move first to a position in alignment with the powder container for being filled and thereafter to a position in alignment with the inhalation channel, whereupon a unit dose will fall by gravity from the dosing recess into the inhalation channel. Thereafter the dose of medicament is inhaled from the inhalation channel. These devices have the drawback that they make overdosing of the medicament possible by allowing the dispensing of a plurality of doses in succession into the inhalation channel, whereby a multiple dose may be drawn by one inhalation.

Attempts have been made to solve the above-mentioned problem by using dispensing systems in which the dosing recess will not be emptied into the inhalation channel by gravity but, instead, the dose of medicament is inhaled directly from the dosing recess, such recesses having been notched into the surface of a metering member having the shape of a cylinder, a cone or a truncated cone, as disclosed in patent publications WO 92/00771 and WO 92/09322. Also in these devices, a metering member having the shape of a cylinder a cone or a truncated cone is disposed in a chamber having precisely the same shape. When the metering member is rotated, the dosing recesses will move first to a position in alignment with the flow container for filling and then to the inhalation channel, which is shaped so that the dosing recess will be emptied under the effect of the air flow being inhaled, and thereafter, having rotated through a full 360°, back to a position in alignment with the flow container: Since the metering member is, for purposes of metering precision, disposed within a chamber of the same shape, and since it has to be rotated through 360°, the metering member may be prone to jamming as powder falls onto the surfaces of the device.

The above problem is at least partly avoided in multidose powder inhalers having a metering member in the form of an axially movable rod equipped with a dosing recess, the metering rod extending through the interior of the medicament container. Such inhalers have been described e.g. in patent publications U.S. Pat. Nos. 5,263,475, 5,765,552 and WO 92/18188. The dosing recess in these devices comprises a groove or a cavity in the surface of the metering rod. These devices suffer from poor filling of the dosing recess and/or poor discharging of the powder from the dosing recess into the air flow, particularly when the powder is not readily flowable.

A dosing recess in the form of a hole extending throughout of the dosing rod is described in U.S. Pat. No. 5,447,151. In this device the dosing hole is first filled with the powder in the medicament container, and subsequently the dosing hole is brought into the air channel where the powder is thrown from the hole to the floor of the air channel by a thrust of a pivotally mounted flap. However, in this device the air stream which is produced by actively breathing in may be insufficient to discharge all the powder from the floor of the air channel into the air stream.

SUMMARY OF THE INVENTION

The object of the present invention is to construct a simple multidose powder inhaler which avoids the above mentioned disadvantages. The device of the invention has good metering accuracy, it is not susceptible to jamming and provides complete discharge of the powdered dose into the breathing air even if used by a patient having reduced inhalation capacity.

This is achieved by providing a device for dispensing powdered medicament by inhalation, comprising a medicament container for receiving a plurality of medicament doses; extending into the interior of the medicament container an axially movable metering rod equipped with a dosing hole, which extends through the rod, for receiving in a first position a metered dose of the powdered medicament and for bringing in a second position the metered dose of the powdered medicament to an air channel where the metered dose of the powdered medicament is discharged to the inhaled air from the dosing hole the metering rod being in the second position.

The device of the invention comprises an axially movable metering rod equipped with a dosing recess in the form of a hole, which extends through the rod in the direction perpendicular to the longitudinal axis of the rod. The metering rod extends into the interior of the medicament container. In the first position of the rod the dosing hole is inside the medicament container and receives a metered dose of the powdered medicament. In the second position the filled dosing hole is brought to an air channel. The metered dose of the powdered medicament is discharged to the inhaled air from the dosing hole while the metering rod is in the second position. It has been found that when the dosing recess is in the form of a hole that extends through the metering rod, the recess is effectively filled as it is dipped into the powder container. Furthermore, the powdered dose is completely dispersed in the inhaled air as the powder is presented to the air channel in the hole through which the inhaled air is conducted. The actually inhaled dose is therefore reproducible at a high level of accuracy. Furthermore, the surfaces rubbing against each other are small whereby the risk of jamming is reduced.

The movement of the rod between the first and the second positions can be implemented in number of ways. In a preferred embodiment of the invention the metering rod extends through the interior of the medicament container. The metering rod is engaged with a device cover that can be moved, e.g. depressed, by the patient. Depressing of the cover causes metering rod to move from one position, e.g. the filling position, to another position, e.g. the inhalation position, or vice versa. However, the metering rod may also be constructed so that the cover is stationary and the metering rod extends through the cover and forms a depressible projection.

The metering rod has preferably a flattened lower portion through which the dosing hole is drilled. This improves the filing of the dosing hole with powder while the metering rod is in the medicament container. The hole is preferably circular or elliptic, but other forms can be contemplated. In any case the hole extends throughout the flat portion of the dosing rod so that in the container the hole is able to receive powder from both sides of the flat portion of the rod.

The lower portion of the metering rod enters the air channel through the wall, e.g. the bottom wall, of the container via a slot adapted to receive the flattened lower portion of the metering rod. The slot is always plugged by the metering rod preventing the flow of the powder from the container. It is also possible to construct the device so that the metering rod does not extend through the whole container, but e.g. only the end portion of the rod having the dosing hole is dipped into the interior of the container via a slot of the container wall for the filling. However, the embodiment where the metering rod extends throughout the whole container, parallel to the longitudinal axis thereof is preferred.

In such embodiment of the invention where the metering rod extends through the container, the metering rod can be easily equipped with one or more agitation members for improving the flow of the powder in the container and for reducing arching of the powder in the container. It is also possible to make the rod rotate slightly every time the device is actuated by providing the rod with a protrusion guided in a groove that is arranged in the cylinder shaped guiding for the rod e.g. inside the upper part of the medicament container in a manner described in U.S. Pat. No. 5,765,552. The slight rotation would enhance the agitation effect of the projections. In the embodiment having a rotating metering rod as described above, the flattened lower portion of the rod with the dosing hole is connected to the rod by a means which allows the rotation of the rod in relation to the non-rotating flattened lower portion of the rod, e.g. by a suitable snapfastening joint.

The metered dose of powder is inhaled from the filled dosing hole as the metering rod is in the inhalation position and the dosing hole in the air channel. It has been found that the powder remains in the dosing hole when the filled dosing bole enters the air channel. The air channel is preferably selected in such manner that substantial part, or preferably all, of the inhaled air flows through the dosing hole as the metering rod is in the inhalation position. This ensures complete discharge of the powdered dose into the breathing air even if the device is used by a patient having reduced inhalation capacity. If a device with a smaller air flow resistance is desired, it is possible to provide the inhalation channel downstream the metering rod with one or more openings in order to get supplementary air flow. Alternatively, the shape of the air channel in the vicinity of the flattened portion of the dosing rod can be modified to allow supplementary air flow around the flattened portion of the dosing rod. The supplementary air flow reduces the flow resistance of the device and may increase the turbulence of the air flow in the air channel.

The preferred embodiment of the invention also comprises an aperture for remnants for removing any powder possibly left in the inhalation channel after the metering rod has returned to the filling position. The aperture of the remnants may lead to a chamber for remnants so as to maintain the remnants inside the inhaler. The aperture for remnants may be closed by the metering rod when the rod is in the inhalation position so as to prevent the powder being inhaled from the chamber of remnants. When the rod moves to the filling position the powder left in the inhalation channel in the vicinity of the moving rod tends to fall into the aperture of remnants by gravity. This may be accomplished by constructing the bottom of the inhalation channel in the vicinity of the moving rod in such a way that the remnants automatically move towards the aperture for remnants by gravity.

Preferably the chamber of remnants is closed below the aperture by a closure member, which is engaged with the metering rod so that the closure member is opened when the metering rod is in the inhalation position and closed when the metering rod is in the filling position.

Alternatively, the lower part of the metering rod may be extended such that it closes the aperture for remnants when the rod is in the inhalation or filling positions, but opens the aperture for remnants when the rod is in a position which is between the filling and inhalation positions. This may be achieved e.g. by providing the flattened lower portion of the metering rod, in the area below the dosing hole, with a broad rectangular opening.

DETAILED DESCRIPTION OF THE INVENTION

The device of the invention is further illustrated below by way of examples, with reference to FIGS. 1 to 8.

Figure 1:
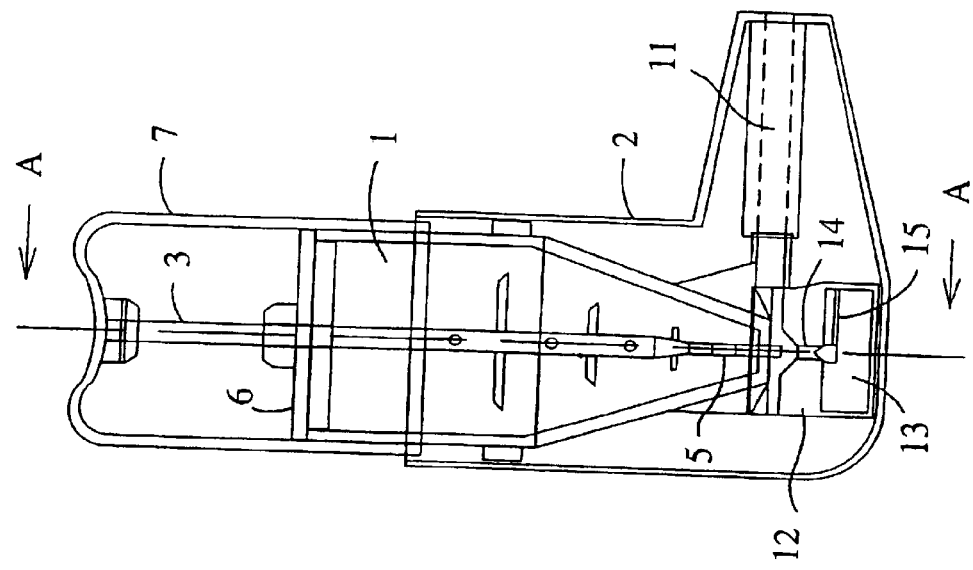
FIG. 1 is a side-view of the device according to a first embodiment of the invention in the filling position.
Figure 2:
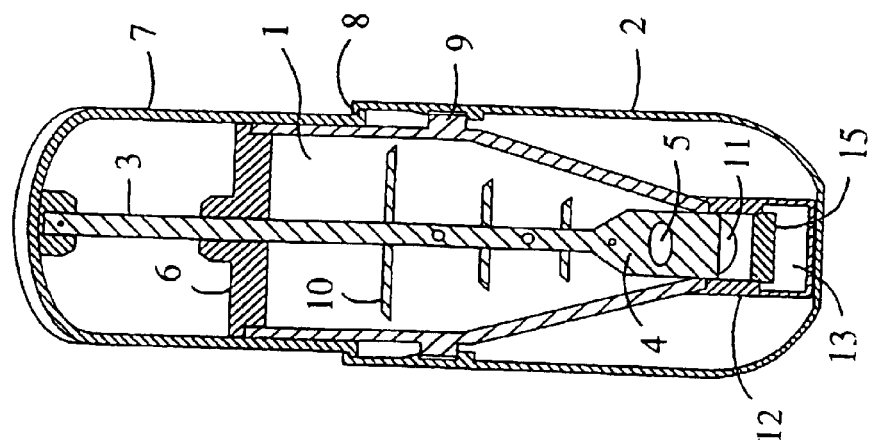
FIG. 2 is a cross sectional view taken along line A—A of FIG. 1.

FIGS. 1 and 2 show a multidose powder inhaler with a medicament container (1) having a certain supply of powdered medicament. The container has a square cross-section and a conical end portion and is secured to an outer casing (2) by snapfastening means. Normally, the container has a supply of medicament for e.g. 200 doses. A dosing rod (3) having a flattened lower portion (4) with a dosing hole (5) is slidably mounted in the container so that it extends through the lid (6) and through the interior of the container. The bottom wall of the container has a slot adapted to receive the flattened lower portion (4) of the dosing rod (3). The upper end of the rod is fixed to a cover (7) such that the rod is movable in its longitudinal direction. The cover is attached to the outer casing (2) by snapfastening means e.g. such as a peripheral lip (8) which puts an upward limit on the movement of the rod. The rod is urged upwards by a spring (shown in FIGS. 5 to 8) bearing firstly against the cover (7) and secondly against the lid (6). The downward limit on the movement of the rod is put by the projection (9) of the container.

The dosing rod has projections (10) for agitation of the powder in the container as the rod slides between its first and second position. This agitation effectively prevents the powder arching ("ceiling effect"), whereby the flow of the powder towards the dosing hole is hindered. It is also possible to make the rod rotate slightly every time the device is actuated by providing the rod with a protrusion guided in a groove that is arranged in the cylinder shaped guiding for the rod e.g. inside the upper part of the medicament container in a manner described in U.S. Pat. No. 5,765,552. The slight rotation would enhance the agitation effect of the projections (10). In the embodiment having a rotating metering rod as described above, the flattened lower portion (4) of the rod (3) with the dosing hole (5) is connected to the rod by a means which allows the rotation of the rod in relation to the non-rotating flattened lower portion of the rod, e.g. by a suitable snapfastening joint.

The outer casing (2) defines a mouthpiece through which air is drawn via an air channel (11). Below the medicament container the air channel is defined by an element (12) containing a chamber (13) for the remnants of powder. The element (12) has an aperture (14) corresponding with the slot of the container bottom so that the flattened lower portion (4) of the dosing rod (3) is guided through the slot to the aperture (14). The air channel extends through the element (12) and through the mouthpiece as a continuous tube. The aperture (14) leads to the chamber for remnants (13) into which remnants of powder left in the inhalation channel tends to fall by gravity. For accomplishing this the bottom of the inhalation channel is, in the vicinity of the aperture, downwardly slanted towards the aperture (14). The chamber of remnants (13) is closed with a closure member in the form of a strip (15) resiliently mounted on the wall of the chamber (13). The strip (15) is engaged with the tip of the metering rod (3) so that the closure member is opened when the metering rod is in the inhalation position and closed when the metering rod is in the filling position.

FIGS. 1 and 2 show the dosing rod (3) in its upper (filling) position wherein the dosing hole (5) of the dosing rod is in the medicament container for receiving powder. The flattened lower portion (4) of the rod extends slightly through the slot of the container bottom thereby preventing the flow of powder through the slot.

Figure 3:
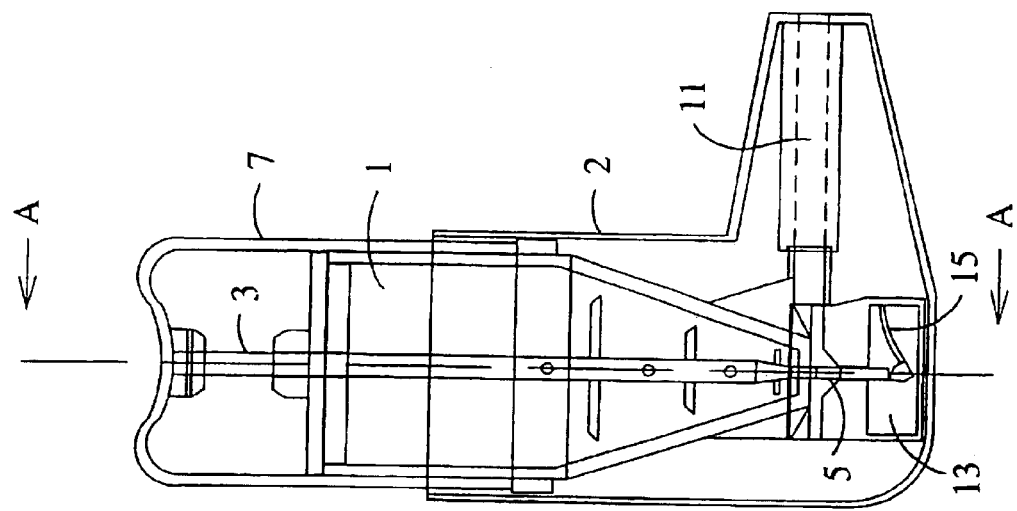
FIG. 3 is a side view of the device of FIG. 1 in the inhalation position.
Figure 4:
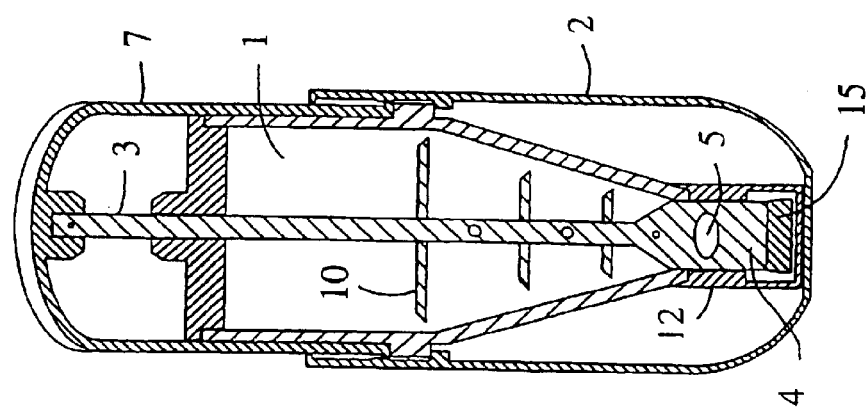
FIG. 4 is a cross sectional view taken along line A—A of FIG. 3.

FIGS. 3 and 4 show the dosing rod in its lower (inhalation) position wherein the cover (7) has been depressed and the dosing hole (5) has moved to the air channel (11). The tip of the flattened portion (4) of the rod has entered the opening (14) and moved the strip (15) to a position where any powder on the strip (15) tends to fall by gravity to the bottom of the chamber of remnants (13). The dosing hole has stopped at the level of the slanted floor of the air channel and the dose is ready to be inhaled via mouthpiece. The inhalation is effected while the cover is depressed. Substantially all inhaled air streams through the dosing hole and the powder is discharged into the air stream directly from the dosing hole.

After inhalation the cover (7) is released and the metering rod (3) returns to the filling position. As the metering rod returns to the filling position, the strip (15) closes the chamber of remnants. At the same time any remnants of the powder left in the slanted portion of the air channel tend to fall through the aperture (14) to the surface of the strip (15) and upon the next return of the metering rod finally into the chamber of remnants.

FIGS. 5 to 8 show an another embodiment of the invention. The air channel (11) has been broadened at the site of the flattened portion (4) of the metering rod (3) in order to provide supplementary air ducts (20) around the flattened portion(4) of the metering rod (3). This reduces the suction resistance felt by the user inhaling through the device. Alternatively, it is also possible to provide supplementary air by providing the air channel (11) downstream the metering rod with one or more openings.

Figure 5:
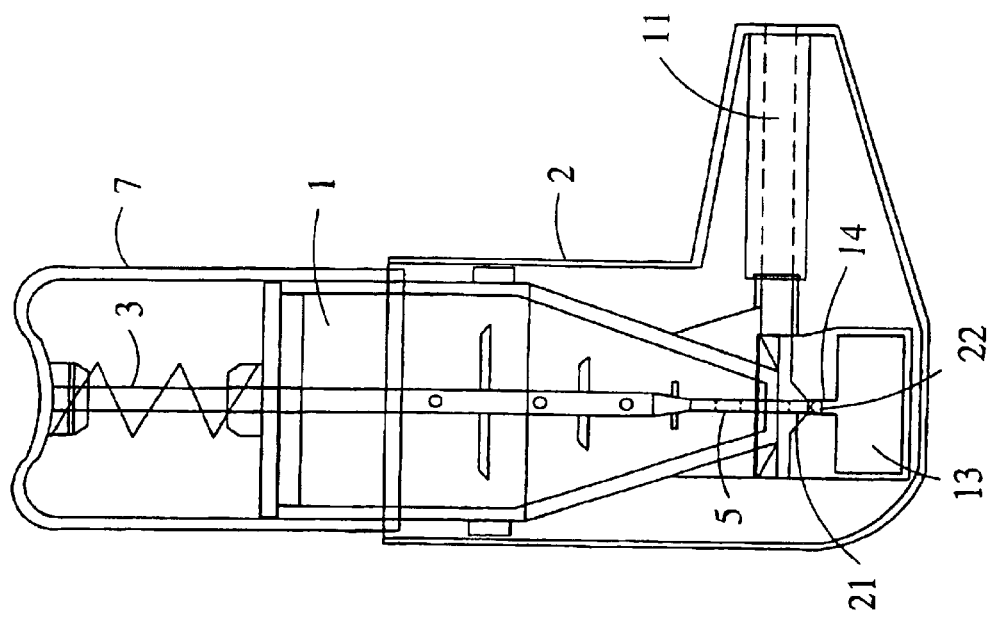
FIG. 5 is a side view of the device according to an another embodiment of the invention in the filling position.
Figure 6:
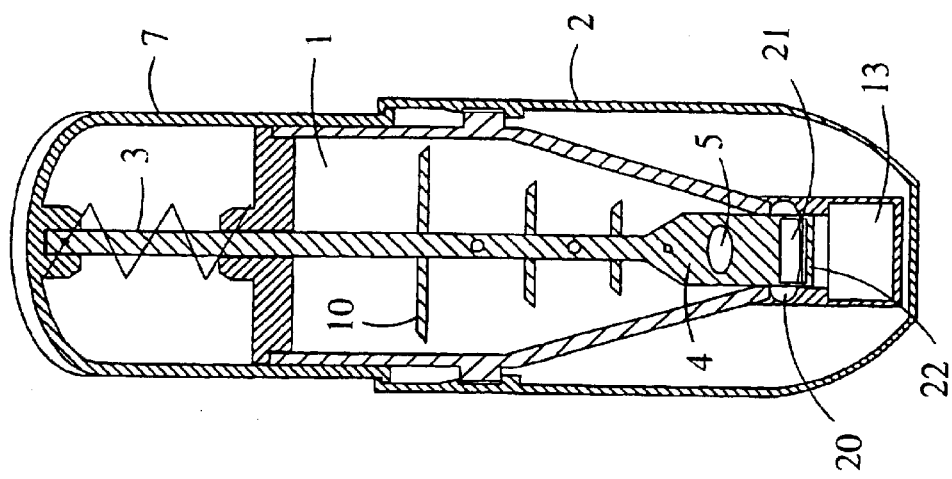
FIG. 6 is a cross sectional front view of the device of FIG. 5.
Figure 7:
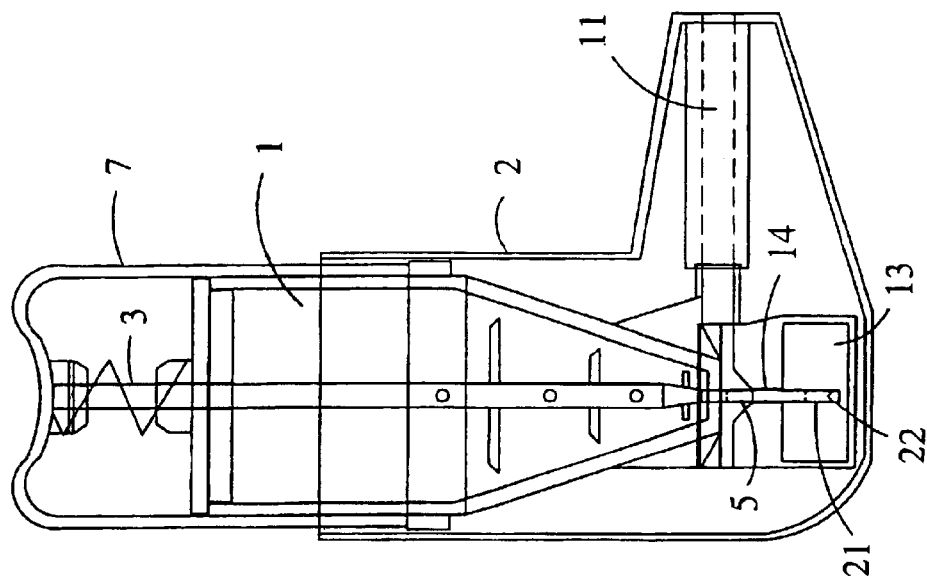
FIG. 7 is a side view of the device of FIG. 5 in the inhalation position.
Figure 8:
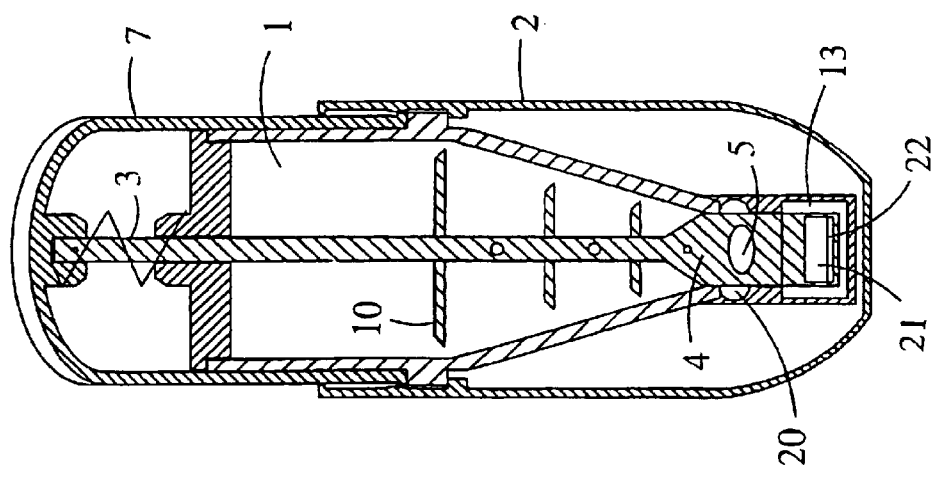
FIG. 8 is a cross sectional front view of the device of FIG. 7.

In the device of FIGS. 5 to 8 the closure strip of the chamber for remnants (13) have been removed. Instead, the lower part of the metering rod (3) has been constructed such that it closes the aperture for remnants (14) when the rod is in the inhalation or filling positions, but opens the aperture for remnants (14) when the rod is in a position which is between the filling and inhalation positions. This is achieved by extending the flattened lower portion (4) of the metering rod (3) in the direction of the chamber of remnants (13) such that the flattened portion closes the aperture (14) also when the rod is in the filling position. The flattened lower portion (4) of the metering rod (3) is further provided with a broad rectangular opening (21), and the lower edge (22) of the opening (21) is downwardly slanted. In FIGS. 5 and 6 the metering rod (3) is in the filling position. The extension of the flattened lower portion (4) of the metering rod (3) slightly enters the aperture (14) and thereby closes the chamber of remnants (13). Powder possibly left on the slanted floor of inhalation channel tends to enter the aperture (14), which is however closed by the lower edge (22) of the opening (21). When the cover (7) in now depressed to transfer the metering rod (3) to the inhalation position, the aperture (14) is temporarily opened and the remnants of powder can enter the chamber (13). When the metering rod (3) has reached its inhalation position (FIGS. 7 and 8), the aperture (14) is again closed by the wall of the flattened portion of the metering rod. When the cover (7) is released and the rod (3) returns to its filling position, the lower edge (22) of the opening (21) again closes the chamber of remnants (13).

Other modifications and variations can be made to the disclosed embodiments without departing from the subject of the invention as defined in the following claims. For example, a counter could be mounted to the inhaler to count the number of pressing of the dosing rod. It is considered to be routine for one skilled in the art to make such modifications to the device of the invention.

What is claimed is:

1. A device for dispensing powdered medicament by inhalation, comprising a medicament container for receiving a plurality of medicament doses; extending into the interior of the medicament container an axially movable metering rod equipped with a dosing hole, which dosing hole extends through the entirety of the metering rod in the direction perpendicular to the longitudinal axis of the rod, the metering rod being movable between a filling position, in which the dosing hole can receive a metered dose of a powdered medicament, and an inhalation position, in which the dosing hole, when filled, is presented to an air channel such that a dose in the dosing hole is ready to be inhaled by the user from the filled dosing hole while the metering rod is in the inhalation position.

2. A device according to claim 1, wherein the metering rod extends through the interior of the medicament container.

3. A device according to claim 1, wherein the metering rod is engaged with a depressible device cover.

4. A device according to claim 1, wherein the metering rod has a flattened lower portion through which the dosing hole extends.

5. A device according to claim 4, wherein the flattened lower portion of the metering rod enters the air channel through the wall of the container via a slot adapted to receive the flattened lower portion of the metering rod.

6. A device according to claim 1, wherein the portion of the metering rod extending into the interior of the medicament container is equipped with one or more agitation members.

7. A device according to claim 1, wherein substantially all inhaled air can be conducted through the dosing hole.

8. A device according to claim 1 comprising an aperture for remnants for removing powder left in the air channel when the metering rod is returned to the filling position.

9. A device according to claim 8, wherein the aperture for remnants leads to a chamber for remnants.

10. A device according to claim 8, wherein the bottom of the air channel is, in the vicinity of the aperture for remnants, downwardly slanted towards the aperture.

11. A device according to claim 8, wherein the aperture for remnants is closed by the metering rod when the metering rod is in the inhalation position.

12. A device according to claim 8, wherein the chamber for remnants is closed by a closure member, which is engaged with the metering rod so that the closure member is opened when the metering rod is in the inhalation position and closed when the metering rod is in the filling position.

13. A device according to claim 8, wherein the lower part of the metering rod closes the aperture for remnants when the rod is in the filling or inhalation positions, but opens the aperture for remnants when the rod is in a position which is between the filling and inhalation positions.

14. A device according to claim 13, wherein the lower part of the metering rod is provided with an opening.

* * * * *